US007892542B2

(12) United States Patent
Gauthier et al.

(10) Patent No.: US 7,892,542 B2
(45) Date of Patent: Feb. 22, 2011

(54) HUMAN ANTI-IDIOTYPIC ANTIBODY FRAGMENTS THAT MIMIC HER-2/NEU

(75) Inventors: Philippe Gauthier, Grabels (FR); André Pelegrin, Montpellier (FR); Mickaël Coelho, Montpellier (FR); Isabelle Teulon, Saint Gely du Fesc (FR)

(73) Assignees: Institut National de la Sante et de la Recherche Medicale (INSERM), Paris (FR); Centre Regional de Lutte Contre le Cancer "Val d'Aurelle-Paul Lamarque", Montpellier Cedex (FR); Universite Montpellier I, Montpellier Cedex (FR)

( * ) Notice: Subject to any disclaimer, the term of this patent is extended or adjusted under 35 U.S.C. 154(b) by 863 days.

(21) Appl. No.: 10/583,034

(22) PCT Filed: Dec. 14, 2004

(86) PCT No.: PCT/IB2004/004096

§ 371 (c)(1), (2), (4) Date: Jun. 15, 2006

(87) PCT Pub. No.: WO2005/061546

PCT Pub. Date: Jul. 7, 2005

(65) Prior Publication Data
US 2007/0298033 A1 Dec. 27, 2007

(30) Foreign Application Priority Data
Dec. 17, 2003 (EP) .................................. 03293196

(51) Int. Cl.
A61K 39/395 (2006.01)
C07K 16/42 (2006.01)
C07K 14/705 (2006.01)
C07K 14/71 (2006.01)

(52) U.S. Cl. ............... 424/131.1; 424/133.1; 424/135.1; 424/184.1; 424/185.1; 530/387.2; 530/387.3; 530/350

(58) Field of Classification Search ............... 424/131.1, 424/133.1, 135.1, 1, 184.1, 185.1; 530/387.2, 530/387.3, 350
See application file for complete search history.

(56) References Cited

U.S. PATENT DOCUMENTS
5,637,677 A 6/1997 Greene et al.

FOREIGN PATENT DOCUMENTS
WO    WO 95/10303    4/1995

OTHER PUBLICATIONS

Fengtian, H. et al., Chin. Med. Sci. J. 17(4): 215-219, 2002.*
Marks, J.D. et al., J. Mol. Biol., 222(3): 581-597, 1991.*
Rudikoff et al, Proc Natl Acad Sci USA 1982 vol. 79 p. 1979.*
MacCallum et al, J. Mol. Biol. (1996) 262, 732-745.*
De Pascalis et al, The Journal of Immunology (2002) 169, 3076-3084.*
Casset et al, (2003) BBRC 307, 198-205.*
Vajdos et al. J. Mol. Biol.(2002) 320, 415-428.*
Holm et al Mol. Immunol., (2007) 44, 1075-1084.*
Chen et al. J. Mol. Biol. (1999) 293, 865-881.*
Wu et al. J. Mol. Biol. (1999) 294, 151-162.*
Tripathi, P.K., et al., Molecular Immunology, 35: 853-863, 1998.*
Cho, H.-S. et al., Nature, 421: 756-760, Feb. 2003.*
Todorovska, A. et al., Journal of Immunological Methods, 248: 47-66, 2001.*
Albanell, J., et al, Mechanism of Action of Anti-Her-2 Monoclonal Antibodies: Scientific Update on Trastuzumab and 2C4, in: New Trends in Cancer for the 21st Century, ed. Llombart-Bosch and Felipo, Kluwer Academic/Plenum, 2003: pp. 253-268.*
Klapper, L.N., et al., Oncogene, 14: 2099-2109, 1997.*
Barbal et al.: "Murine monoclonal anti-idiotypic antibody as a surrogate antigen . . . ", Int'l Journal of Cancer, vol. 92, 2001, pp. 88-95—XP002285279 cited in the abstract.
Matti et al.: "Development of a single chain Fv from a human anti-ID monoclonal antibody that mimics the GD2 antigen . . . ", Proceedings Of The American Assoc. for Cancer Research, vol. 43, Mar. 2002, p. 970—XP002285280.
Leung et al.: "A human and a mouse anti-idiotypic antibody specific for human T14+ anti-DNA . . . ", GENE, vol. 255, 2000, pp. 373-380—XP004217652.
Durrant et al.: "Human anti-idiotypic antibodies can be a good immunogens as they target Fc . . . ", Int'l Journal of Cancer, vol. 92, No. 3 Mar. 1, 2001 pp. 414-420; XP002285281.
Saleh et al.: "Generation of human anti-idiotypic antibody that mimics the GD2 antigen", The Journal of Immunology, vol. 151, No. 6, Sep. 15, 1993, pp. 3390-3398—XP002091381.
Saha et al.: "Murine dendritic cells pulsed with an anti-idiotype antibody induce antigen-idiotype antibody . . . ", Cancer Research, vol. 63, Jun. 1, 2003, pp. 2844-2854—XP002285282.
Coelho et al.: "Isolation and characterization of human anti-idiotypic scFv used as a surrogate tumour . . . ", British Journal of Cancer, vol. 90, No. 10, May 17, 2004 pp. 2032-2041, XP002317270.

* cited by examiner

*Primary Examiner*—Alana M. Harris
*Assistant Examiner*—Anne L Holleran
(74) *Attorney, Agent, or Firm*—B. Aaron Schulman; Terry L. Wright; Stites & Harbison PLLC

(57) ABSTRACT

This invention relates to human anti-idiotypic antibody fragments, especially scFv, characterized by the ability to mimic Her-2/neu tumor associated antigen. These antibody fragments are promising candidates for active immunotherapy for cancer patients positive for Her-2/neu.

13 Claims, 7 Drawing Sheets

ScFv 40

Figure 1:
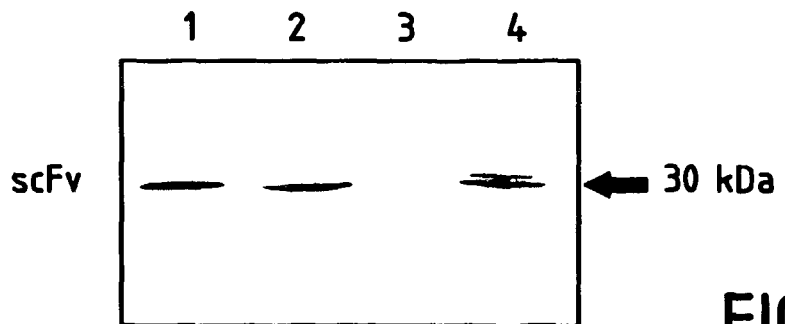

| FR1 | CDR1 | FR2 |
|---|---|---|
| EVQLLESGGGLVQPGGSLRLSCAASGFTFS | S YAMS | WVRQAPGKGLEWVS AISG |

| CDR2 | FR3 | CDR3 |
|---|---|---|
| SGGSTYYADSVKG | RFTISRDNSKNTLYLQMNSLRAEDTAVYYCAK | NYQIHP |

| FR4 | Linker | FR1 |
|---|---|---|
| FDYWGQGTLVTVSR | GGGGSGGGGSGGGGS | SELTQDPAVSVALGQTVRITC QG |

| CDR1 | FR2 | CDR2 | FR3 |
|---|---|---|---|
| DSLRSYYAS | WYQQKPGQAPVLVIY | GKNNRPS | GIPDRFSGSSSGNTASLTITGAQAEDE |

| CDR3 | FR4 |
|---|---|
| ADYYC NSSDPDQLL | VVFGGGTKLTVLG |

ScFv 69

| FR1 | CDR1 | FR2 |
|---|---|---|
| EVQLLESGGGLVQPGGSLRLSCAASGFTFS | S YAMS | WVRQAPGKGLEWVS AISG |

| CDR2 | FR3 | CDR3 |
|---|---|---|
| SGGSTYYADSVKG | RFTISRDNSKNTLYLQMNSLRAEDTAVYYCAK | NVHIQP |

| FR4 | Linker | FR1 |
|---|---|---|
| FDYWGQGTLVTVSR | GGGGSGGGGSGGGGS | SELTQDPAVSVALGQTVRITC QG |

| CDR1 | FR2 | CDR2 | FR3 |
|---|---|---|---|
| DSLRSYYAS | WYQQKPGQAPVLVIY | GKNNRPS | GIPDRFSGSSSGNTASLTITGAQAEDE |

| CDR3 | FR4 |
|---|---|
| ADYYC NSSEPTPPR | VVFGGGTKLTVLG |

FIG. 9

SEQUENCE LISTING

```
<160> NUMBER OF SEQ ID NOS: 18

<210> SEQ ID NO 1
<211> LENGTH: 241
<212> TYPE: PRT
<213> ORGANISM: Homo sapiens

<400> SEQUENCE: 1

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
                35                  40                  45
Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Tyr Gln Ile His Pro Phe Asp Tyr Trp Gly Gln Gly Thr
            100                 105                 110

Leu Val Thr Val Ser Arg Gly Gly Gly Ser Gly Gly Gly Ser
        115                 120                 125

Gly Gly Gly Gly Ser Ser Glu Leu Thr Gln Asp Pro Ala Val Ser Val
130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Gly Asn Thr Ala Ser Leu Thr Ile Thr Gly
        195                 200                 205

Ala Gln Ala Glu Asp Glu Ala Asp Tyr Tyr Cys Asn Ser Ser Asp Pro
210                 215                 220

Asp Gln Leu Leu Val Phe Gly Gly Gly Thr Lys Leu Thr Val Leu
225                 230                 235                 240

Gly

<210> SEQ ID NO 2
<211> LENGTH: 241
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asn Val His Ile Gln Pro Phe Asp Tyr Trp Gly Gln Gly Thr
            100                 105                 110

Leu Val Thr Val Ser Arg Gly Gly Gly Ser Gly Gly Gly Ser
        115                 120                 125

Gly Gly Gly Gly Ser Ser Glu Leu Thr Gln Asp Pro Ala Val Ser Val
130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
```

-continued

```
                    165                 170                 175
Leu Val Ile Tyr Gly Lys Asn Asn Arg Pro Ser Gly Ile Pro Asp Arg
            180                 185                 190

Phe Ser Gly Ser Ser Gly Asn Thr Ala Ser Leu Thr Ile Thr Gly
        195                 200                 205

Ala Gln Ala Glu Asp Glu Ala Asp Tyr Tyr Cys Asn Ser Ser Glu Pro
    210                 215                 220

Thr Pro Pro Arg Val Val Phe Gly Gly Gly Thr Lys Leu Thr Val Leu
225                 230                 235                 240

Gly

<210> SEQ ID NO 3
<211> LENGTH: 6
<212> TYPE: PRT
<213> ORGANISM: Homo sapiens

<400> SEQUENCE: 3

Asn Tyr Gln Ile His Pro
1               5

<210> SEQ ID NO 4
<211> LENGTH: 6
<212> TYPE: PRT
<213> ORGANISM: Homo sapiens

<400> SEQUENCE: 4

Asp Pro Asp Gln Leu Leu
1               5

<210> SEQ ID NO 5
<211> LENGTH: 6
<212> TYPE: PRT
<213> ORGANISM: Homo sapiens

<400> SEQUENCE: 5

Asn Val His Ile Gln Pro
1               5

<210> SEQ ID NO 6
<211> LENGTH: 6
<212> TYPE: PRT
<213> ORGANISM: Homo sapiens

<400> SEQUENCE: 6

Glu Pro Thr Pro Pro Arg
1               5

<210> SEQ ID NO 7
<211> LENGTH: 11
<212> TYPE: PRT
<213> ORGANISM: Homo sapiens

<400> SEQUENCE: 7

Cys Ala Lys Lys Lys Ile Gly Pro Phe Asp Tyr
1               5                   10

<210> SEQ ID NO 8
<211> LENGTH: 12
<212> TYPE: PRT
<213> ORGANISM: Homo sapiens

<400> SEQUENCE: 8
```

-continued

Asn Ser Ser Pro Arg Pro Asn Ala Pro Val Val Phe
1               5                   10

<210> SEQ ID NO 9
<211> LENGTH: 12
<212> TYPE: PRT
<213> ORGANISM: Homo sapiens

<400> SEQUENCE: 9

Cys Ala Lys Asn Tyr Gln Ile His Pro Phe Asp Tyr
1               5                   10

<210> SEQ ID NO 10
<211> LENGTH: 12
<212> TYPE: PRT
<213> ORGANISM: Homo sapiens

<400> SEQUENCE: 10

Asn Ser Ser Asp Pro Asp Gln Leu Leu Val Val Phe
1               5                   10

<210> SEQ ID NO 11
<211> LENGTH: 12
<212> TYPE: PRT
<213> ORGANISM: Homo sapiens

<400> SEQUENCE: 11

Cys Ala Lys Asn Val His Ile Gln Pro Phe Asp Tyr
1               5                   10

<210> SEQ ID NO 12
<211> LENGTH: 12
<212> TYPE: PRT
<213> ORGANISM: Homo sapiens

<400> SEQUENCE: 12

Asn Ser Ser Glu Pro Thr Pro Pro Arg Val Val Phe
1               5                   10

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence:primer

<400> SEQUENCE: 13
tactacgcag actccgtgaa g                                          21

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence:primer

<400> SEQUENCE: 14
gaattttctg tatgagg                                               17

<210> SEQ ID NO 15
<211> LENGTH: 5
<212> TYPE: PRT
<213> ORGANISM: Homo sapiens

<400> SEQUENCE: 15

```
Ser Tyr Ala Met Ser
1               5

<210> SEQ ID NO 16
<211> LENGTH: 11
<212> TYPE: PRT
<213> ORGANISM: Homo sapiens

<400> SEQUENCE: 16

Gln Gly Asp Ser Leu Arg Ser Tyr Tyr Ala Ser
1               5                   10

<210> SEQ ID NO 17
<211> LENGTH: 12
<212> TYPE: PRT
<213> ORGANISM: Homo sapiens

<400> SEQUENCE: 17

Ser Gly Gly Thr Tyr Tyr Ala Asp Ser Val Lys Gly
1               5                   10

<210> SEQ ID NO 18
<211> LENGTH: 7
<212> TYPE: PRT
<213> ORGANISM: Homo sapiens

<400> SEQUENCE: 18

Gly Lys Asn Asn Arg Pro Ser
1               5
```

HUMAN ANTI-IDIOTYPIC ANTIBODY FRAGMENTS THAT MIMIC HER-2/NEU

The present invention relates to human anti-idiotypic antibody fragments that mimic the HER-2/neu tumor-associated antigen.

For active cancer immunotherapy, the tumor-associated antigen (TAA) HER-2/neu is a promising cancer vaccine candidate since it is overexpressed on the surface of a number of human cancers, but its expression in normal tissue is restricted. It has been shown to be immunogenic in animals and in humans, and it is targetable by monoclonal antibodies. This 185-kDa transmembrane phosphoglycoprotein consists of a cysteine-rich extracellular domain (ECD) that functions in ligand binding and an intracellular cytoplasmic domain with kinase activity. Moreover, HER-2/neu is a member of the epidermal growth factor receptor family. Cancers in which HER-2/neu protein overexpression occurs include human adenocarcinomas such as breast (in 20% to 40% of intraductal carcinomas) or ovary (in 30%). Although overexpression has been linked to more aggressive disease and a poorer prognosis in node-positive breast cancer, it has also been established that it is related to a favorable prognosis in some patients with stage I breast tumors that contain inflammatory infiltrates which may represent an immune response directed against autologous cancer cells (Rilke et al. 1991). One hypothesis is that the better outcome in these patients may be related to the generation of an HER-2/neu-specific immune response which could directly or indirectly limit further growth and metastasis. Different investigations defining HER-2/neu-specific immunity in patients with cancer indicate that high levels of both T-cell and antibody immunity exists in some patients, even if it is low or lacking in the majority of them (Disis et al. 1994—Fisk et al. 1995—Peoples et al. 1995). This strongly suggests that immunological tolerance exists, probably related to the oncofetal origin of HER-2/neu, and that it represents a barrier to effective vaccination against this antigen (Nanda et al. 1995—Disis et al. 1998). Furthermore, different studies have proven that anti-HER-2/neu monoclonal antibodies (mAbs) can be effective in eradicating tumors (Baselga et al. 2001).

These findings have stimulated further studies to test vaccine strategies to induce and increase immunity to HER-2/neu for the treatment of breast cancer or for the prevention of recurrent disease. Effective vaccine strategies must circumvent tolerance. For this reason, methods to break this tolerance, such as presenting the critical epitope in a different molecular environment to the tolerized host, have been developed. Several studies have evaluated whether tolerance to HER-2/neu could be circumvented by immunization with either peptide-based vaccines (Disis et al. 1996—Dakappagari et al., 2000—Disis et al. 2002) or DNA (Concetti et al. 1996—Di Carlo et al. 2001—Pilon et al. 2001). Some encouraging results were obtained but with persistence of problems such as the weak immunogenicity of the peptides or the potential adverse effect of administering plasmid DNA encoding a functional oncogene.

Among the vaccine strategies developed to overcome immune tolerance to self-proteins, vaccination with anti-idiotypic antibodies has been described as a promising approach for treatment of several malignant diseases.

Anti-idiotypic antibodies are antibodies directed against the antigen-combining region or variable region (called the idiotype or Id) of another antibody molecule. In theory, based on Jerne's network model of idiotypic relationships (Jerne 1974—Jerne et al., 1982), immunization with an antibody molecule expressing a paratope (antigen-combining site) for a given antigen should produce a group of anti-antibodies, some of which share with the antigen a complementary structure to the paratope. Immunization with a subpopulation of the anti-idiotypic antibodies should in turn produce a subpopulation of antibodies or immune cell subsets that are reactive to the initial antigen.

Active immunization with tumor-specific Id vaccines has very early been shown to inhibit tumor growth in animals (Kennedy et al. 1985).

U.S. Pat. No. 5,766,588 proposes methods which utilize anti-idiotypic antibodies for tumor immunotherapy or immunoprophylaxis. However, the anti-idiotypic antibodies described in this U.S. patent are murine antibodies that are secreted by hybridomas.

Anti-Id antibodies that functionally mimic an antigen have been used for the treatment of colorectal carcinoma [CEA, (Foon et al. 1999)], B and T-cell lymphoma [gp72, (Kwak et al. 1992) and gp37 (Bhattacharya-Chatterjee et al. 1988), respectively], and for the treatment of melanoma by triggering an active immune response against the disialoganglioside GD2 (Foon et al. 2000). Anti-diotypic mAbs mimicking the human high molecular weight melanoma-associated antigen have also been tested in a clinical trial to implement active specific immunotherapy (Mitttelman et al. 1990).

In 1998, carcinoembryonic antigen (CEA) mimicry by an anti-idiotypic single chain variable fragment (scFv) constructed from a murine mAb was published with convincing results regarding the level of the humoral response raised in mice (Tripathi et al. 1998). More recently, a study from the same group described the use of a murine monoclonal anti-Id antibody as a surrogate antigen for human HER-2/neu (Baral et al. 2001).

However, most of the antibodies tested in these prior studies are murine antibodies, which are likely to provoke undesirable side effects in humans. Repeated injections in humans of a "foreign" antibody, such as a mouse antibody, may indeed lead to harmful hypersensitivity reactions, i.e., anti-mouse antibody (HAMA) or an anti-idiotypic response. The HAMA response makes repeated administrations less effective due to an increased rate of clearance from the patient's serum and/or allergic reactions by the patient. This problem can, in principle, be avoided by making antibodies that are not recognized as foreign by the human immune system.

Yet little is known about human anti-idiotypic antibodies, as mentioned in Leung et al., 2000.

The present invention thus fulfils a need by providing human anti-idiotypic antibody fragments that mimic the Her-2/neu tumor-associated antigen, particularly useful in an active immunotherapy for cancer patients positive for Her-2/neu.

The inventors more specifically selected by phage display and characterized anti-idiotypic scFv directed against the F(ab')$_2$ fragments of a known anti-Her-2/neu antibody. Data obtained from an in vivo study using different immunization schedules indicate that these human anti-Id scFv can induce an effective anti-HER-2/neu humoral response.

On this basis, a subject of the present invention is a human anti-idiotypic fragment characterized by the ability to mimic Her-2/neu tumor associated antigen.

Another subject of the invention is a pharmaceutical composition comprising such antibody fragment, in association with a pharmaceutically acceptable carrier.

A further subject of the invention is the use of such antibody fragment for the prevention or treatment of a tumor wherein Her-2/neu is overexpressed.

Another subject of the invention is an ex vivo method for preparing antigen-presenting cells (APCs), such as dendritic cells, useful for inducing Her-2/neu specific protective anti-tumor immunity, which method comprises contacting an APC with such antibody fragment. The APC is then useful for the prevention or treatment of a tumor wherein Her-2/neu is overexpressed.

General Definitions

According to the present invention, "antibody" or "immunoglobulin" have the same meaning, and will be used equally in the present invention. In natural antibodies, the two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Preferably, the antibody is an IgG such as $IgG_1$, $IgG_2$, $IgG_3$ or $IgG_4$. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors. The Fv fragment is the N-terminal part of the Fab fragment of an immunoglobulin consisting of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. The CDR refers to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. FR refers to amino acid sequences interposed between CDRs.

The invention provides an isolated functional antibody Fab or scFv fragment that mimics HER-2/neu. Preferably, the antibody fragment of the invention is a scFv fragment.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

By "purified" and "isolated" it is meant, when referring to a polypeptide (i.e. the antibody fragment of the invention) or a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

"Function-conservative variants" are those in which a given amino acid residue in a protein has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide. Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, most preferably at least 85%, and even more preferably at least 90%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

"Pharmaceutically" or "pharmaceutically acceptable" refer to molecular entities and compositions that do not produce an adverse, allergic or other untoward reaction when administered to a mammal, especially human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Production of Anti-Idiotypic Antibody Fragments of the Invention

The present invention provides human anti-idiotype antibody fragments characterized by the ability to mimic Her-2/neu tumor associated antigen.

Human antibody fragments can be isolated from phage display libraries, by-passing hybridoma technology (Winter et al. 1994, U.S. Pat. No. 5,223,409). The fragments of the invention, that are able to mimic Her-2/neu antigen, are thus preferably produced by phage display, according to a technique as described in Goletz et al., 2002 for instance.

According to the phage display technique, gene segments encoding the antigen-binding variable or V domains of antibodies are fused to genes encoding the coat protein of a bacteriophage. Bacteriophage containing such gene fusions are used to infect bacteria, and the resulting phage particles have coats that express the antibody-like fusion protein, with the antigen-binding domain displayed on the outside of the bacteriophage. A collection of recombinant phage, each displaying a different antigen-binding domain on its surface, is known as a phage display library. In much the same way that antibodies specific for a particular antigen can be isolated from a complex mixture by affinity chromatography, phage expressing antigen-binding domains specific for a particular antigen can be isolated by selecting the phage in the library for binding to that antigen. The phage particles that bind are recovered and used to infect fresh bacteria. Each phage isolated in this way produces a monoclonal antigen-binding particle analogous to a monoclonal antibody. The genes encoding the antigen-binding site, which are unique to each phage, can then be recovered from the phage DNA. When the genes encoding antibody fragment are introduced into a suitable host cell line, such as bacteria, the transfected cells can secrete antibody fragments.

The ETH-2 synthetic human antibody phage library, as described below (Example section), has proved very useful in that respect.

In a preferred embodiment, the Fab or scFv antibody fragments according to the invention are thus obtainable by phage display. In this way, antibody fragments that are entirely human in origin can be obtained. Fragments of interest may advantageously be produced and directed against the F(ab')$_2$ of the known anti-Her-2/neu antibody called trastuzumab (marketed as Herceptin® by Roche).

A preferred fragment of the invention comprises a sequence SEQ ID No: 3 (NYQIHP) in the CDR3 region of the $V_H$ domain and a sequence SEQ ID No: 4 (DPDQLL) in the CDR3 region of the $V_L$ domain.

Another preferred fragment of the invention comprises a sequence SEQ ID No: 5 (NYHIQP) in the CDR3 region of the $V_H$ domain and a sequence SEQ ID No: 6 (EPTPPR) in the CDR3 region of the $V_L$ domain.

Function-conservative variants or antibody fragments with homologous sequences are also encompassed.

Preferably, it is provided an scFv fragment.

Such scFv fragment preferably comprises a sequence SEQ ID No: 3 in the CDR3 region of the $V_H$ domain and a sequence SEQ ID No: 4 in the CDR3 region of the $V_L$ domain.

Another preferred scFv fragment comprises a sequence SEQ ID No: 5 in the CDR3 region of the $V_H$ domain and a sequence SEQ ID No: 6 in the CDR3 region of the $V_L$ domain.

Fragments designated scFv 40 and svFv 69, that comprise the amino acid sequence SEQ ID No: 1 and SEQ ID No: 2 respectively, are most preferred, as shown on FIG. 9.

Function-conservative variants or antibody fragments having homologous sequences are also encompassed.

Knowing the amino acid sequence of the desired fragment, one skilled in the art can readily produce scFv 40 or scFv 69 fragments, by standard techniques for production of polypeptides. For instance, they can be synthesized using well-known solid phase method (Merrifield et al., 1962 and 1963; Tam et al. 1983), preferably using a commercially available peptide synthesis apparatus (such as that made by Applied Biosystems, Foster City, Calif.) and following the manufacturer's instructions.

Alternatively, the antibody scFv fragments can be synthesized by recombinant DNA techniques as is now well-known in the art (Maniatis et al., 1982). For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Multimerization of the Fragments

In another embodiment of the invention, it is provided multimers, especially dimers or trimers, of the anti-idiotypic antibody fragments described above.

Multimers can be obtained by genetic engineering, using linker sequences between the Fab or scFv sequences defined above.

The linker sequences may include a leucine zipper, e.g. as described in de Kruif and Logtenberg, 1996 or Pack et al., 1993.

Other cross-linked multimers of the antibody fragments can be designed, as well as linear multimer, in particular in a linear head-to-tail manner (Miller et al., 2003).

Multimers are particularly advantageous to diminish elimination through kidneys and to increase stability and half-life of the fragments of interest.

It should thus be understood that, in the whole description of the present invention, all formulations (i.e. pharmaceutical compositions), uses, or processes that are described in reference with Fab or scFv fragments also apply to multimers of these fragments.

Pharmaceutical Compositions

The present invention further encompasses preparing pharmaceutical compositions useful for preventing or treating a tumor that overexpresses Her-2/neu. Examples of pharmaceutical formulations are provided hereafter.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the anti-idiotype antibody fragment or multimer thereof may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An anti-idiotype antibody fragment or multimer thereof can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions are administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The anti-idioype antibody fragment may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of the antibody fragments into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Immunotherapy

Patients having tumors may be treated therapeutically by immunization with the anti-idiotype antibody fragments of the present invention whereas patients with a disposition for the tumor may be treated immunoprophylactically by such immunization. The anti-idiotypic antibody fragments may be formulated with a suitable adjuvant in order to enhance the immunological response. These adjuvants may include, but are not limited to, mineral gels, e.g. aluminium hydroxide; surface active substances such as lysolecithin, pluroic polyols; polyanions; peptides; oil emulsions; and potentially useful human adjuvants such as BCG (bacilli Calmette-Guerin) and *corynebacterium*. Other improved adjuvant systems may be used, such as those reviewed in McCluskie and Weeratan, 2001.

A subject of the present invention is thus the use of an anti-idiotype antibody fragment as defined above, or a multimer thereof, for the preparation of a medicament for the prevention or treatment of a tumor wherein Her-2/neu is overexpressed.

Another subject of the invention is a method for the preparation of a medicament for the prevention or treatment of a tumor wherein Her-2/neu is overexpressed, in a patient, in need thereof, which method comprises administering to said patient a therapeutically effective amount of an anti-idiotype antibody fragment thereof, or a multimer thereof.

A therapeutically effective amount is an amount sufficient for the tumor to show a significant reduction, of at least 10%, preferably at least 30%, preferably at least 50%, preferably at least 80%, or it is an amount sufficient for significantly reducing the risk of developing such tumor.

Tumors wherein an overexpression of Her2/neu is observed include adenocarcinomas, such as breast cancer, ovary cancer, uterus cancer, stomach cancer and lung cancer.

The pharmaceutical compositions containing human anti-idiotype antibody fragments, that mimic Her-2/neu, are thus promising candidates as vaccines to generate or enhance a protective immune response in patients that are affected with tumors overexpressing Her-2/neu.

Antigen-Presenting Cell Therapy

In another embodiment of the invention, it is provided a method for inducing Her-2/neu-specific protective antitumor immunity, which method comprises:

a) ex vivo contacting an antigen-presenting cell (APC) with an anti-idiotype antibody fragment as defined above;

b) administering the APC so treated to a patient in need of such treatment.

Step a) is also called "pulsing" of the cells with the antibody fragment (Saha et al., 2003).

Another subject of the invention is an ex vivo method for preparing APCs useful for inducing HER-2/neu-specific protective antitumor immunity, which method comprises contacting or pulsing an antigen-presenting cell with an anti-idiotype antibody fragment as defined above.

Preferably the APC is a dendritic cell, in particular a bone-marrow derived dendritic cell. Advantageously, the APC is from the patient to whom it is intended to be readministered.

The isolated APCs so treated are also part of the present invention.

The invention further provides the use of such APCs for the preparation of a medicament for the prevention or treatment of a tumor wherein Her-2/neu is overexpressed.

The formulation (pharmaceutical compositions), uses or processes that are described above in reference to the Fab or scFv fragments also apply to such APCs.

The below figures and examples illustrate the present invention without restricting its scope.

LEGENDS OF FIGURES

FIG. 1 represents an immunoblot analysis of several periplasmic fractions containing antibodies after induction with 1 mM IPTG of single ampicillin-resistant infected *E. coli* HB2151 colonies. Lane 1: clone 39; lane 2: clone 40; lane 3: clone 92; lane 4: clone 69. After size fractionation on 12.5% SDS-PAGE, protein extracts were blotted onto nitrocellulose. The immunoblot was developed with HRP-conjugated M2 anti-FLAG mAb (1:2000) followed by addition of the 4-chloro-1-naphtol substrate.

Figure 2:
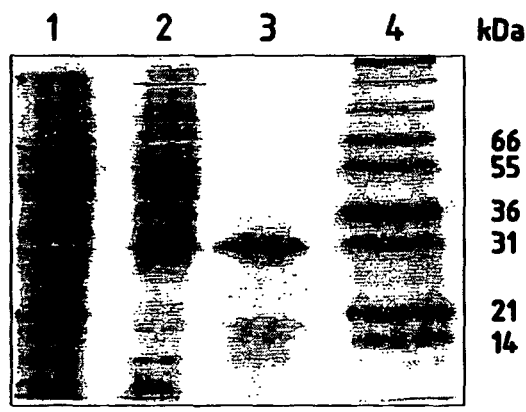

FIG. 2 shows a SDS-PAGE gel. The purity of anti-Id scFv 69 at each step of purification was controlled on 12.5% SDS-PAGE gel followed by silver staining. Lane 1: non-purified periplasmic fraction. Lane 2: purified periplasmic fraction on Hitrap Ni-activated chelating column. Lane 3: purified periplasmic fraction on Hitrap Ni-activated chelating column followed by a gel-filtration purification on a Superdex 75 column. Lane 4: standard molecular mass markers.

Figure 3:
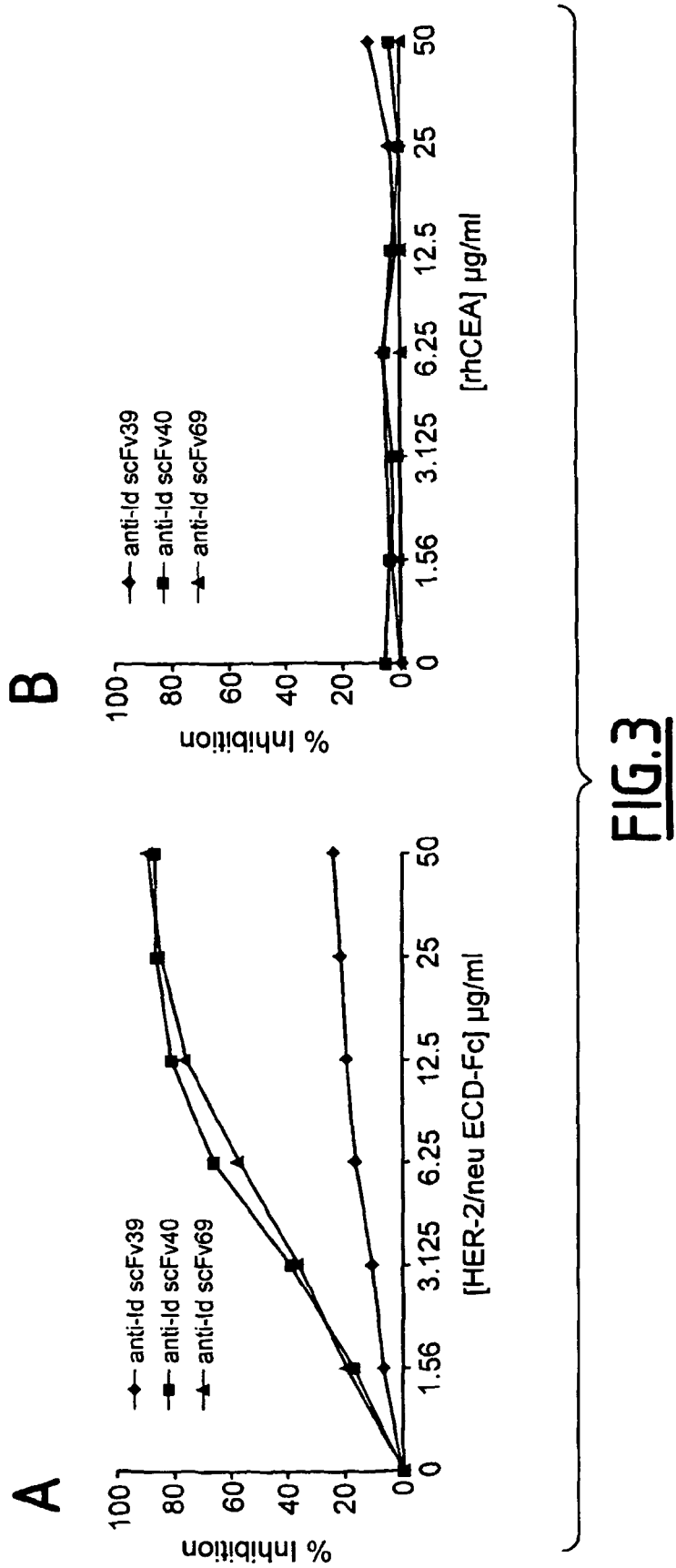

FIGS. 3A and 3B are graphs that show inhibition of purified soluble scFv 39, 40 and 69 binding on trastuzumab F(ab')$_2$ fragments by (A) HER-2/neu ECD-Fc fusion protein and (B) rhCEA, using a competitive ELISA. Increasing amounts of inhibitor were mixed with either anti-Id scFv 39, 40, or 69 used at a dilution giving an $A_{490}$ ranging from 1 to 1.5 in ELISA. The incubation on trastuzumab F(ab')$_2$ fragments for 1.5 h was followed by the detection of scFv binding with HRP-conjugated M2 anti-FLAG mAb (1:2000). The results obtained are expressed as percent inhibition at each concentration of inhibitor.

Figure 4:
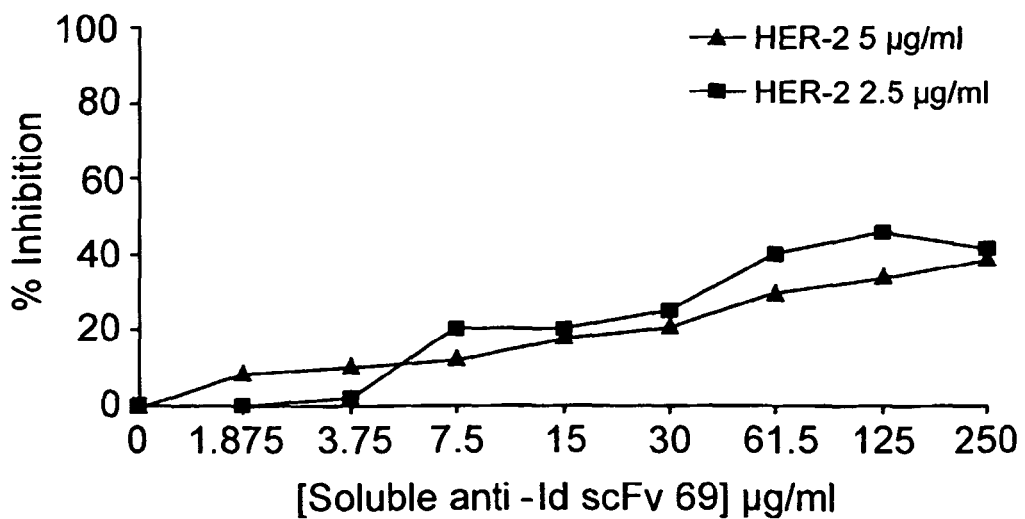

FIG. 4 is a graph that shows inhibition of HER-2/neu ECD-Fc fusion protein binding on trastuzumab F(ab')$_2$ fragments by purified scFv 69 by competitive ELISA. Increasing amounts of inhibitor were mixed with HER-2/neu ECD-Fc fusion protein at 2.5 or 5 µg/ml and incubated with trastuzumab F(ab')$_2$ fragments for 1.5 h. HER-2/neu ECD-Fc fusion protein binding was then detected with peroxidase-conjugated anti-HER-2/neu FRP5 mAb (1:3000). The results obtained are expressed as percent inhibition at each concentration of inhibitor.

Figure 5:
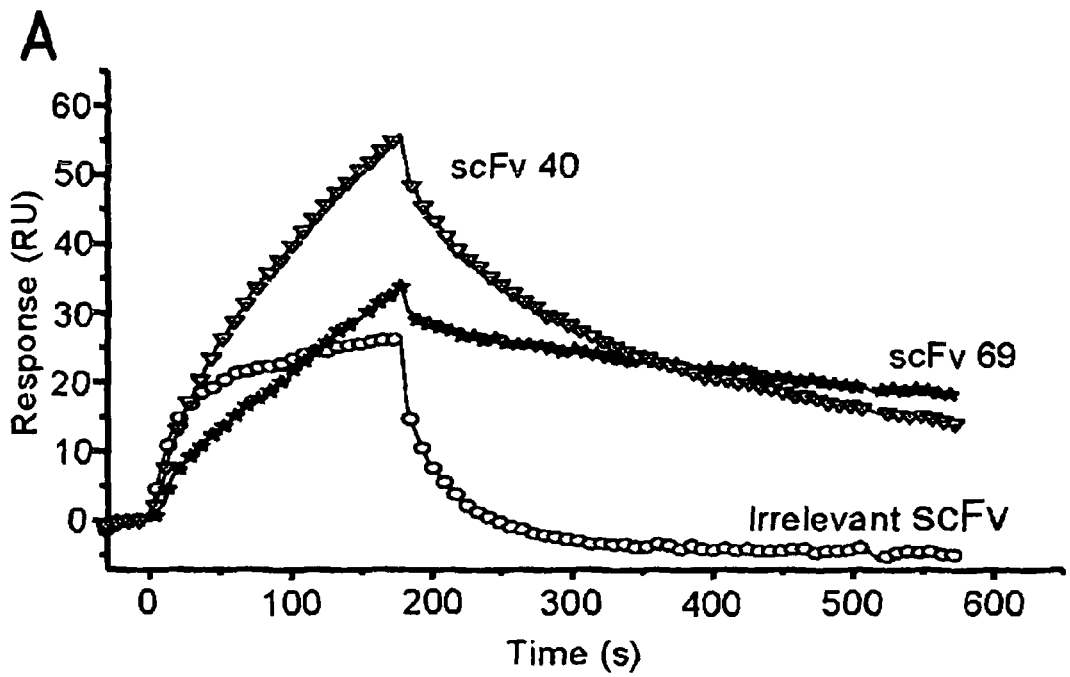
Figure 5:
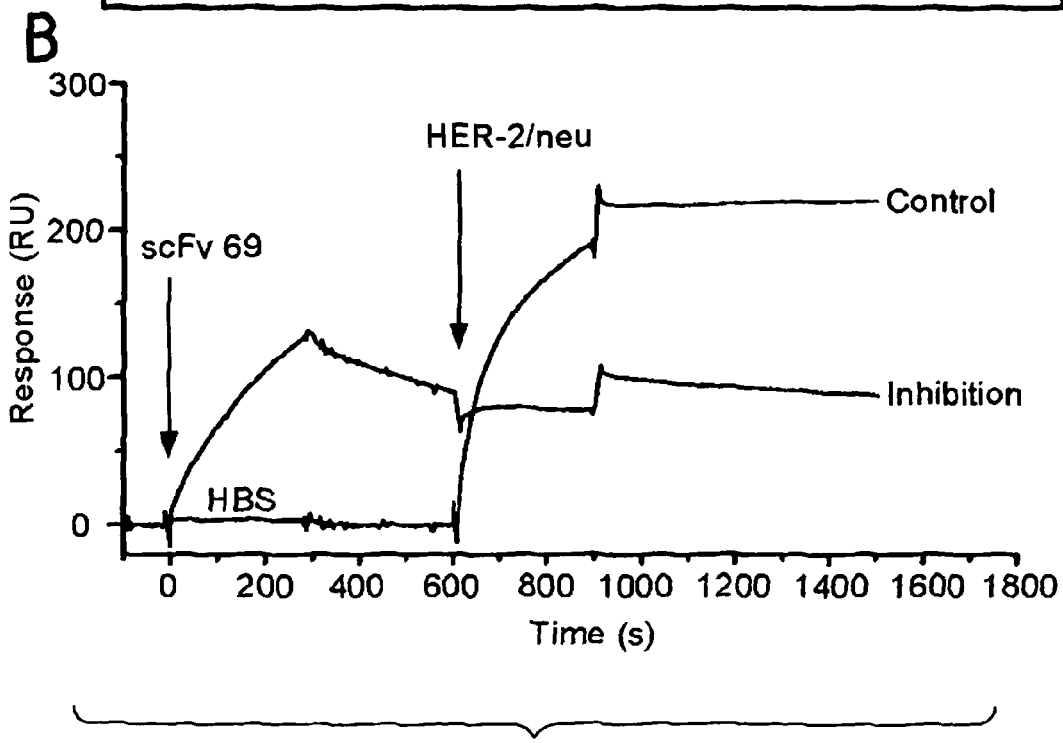

FIGS. 5A and 5B are analysis of BIACORE experiments: (A) Binding kinetics of anti-Id scFv 40, 69, and irrelevant scFv on trastuzumab F(ab')$_2$ fragments immobilized on a CM5 sensor chip and equilibrium affinity constants (inserted Table), (B) Inhibition of HER-2/neu ECD-Fc fusion protein binding on trastuzumab F(ab')$_2$ fragments immobilized on a CM5 sensor chip by anti-Id scFv 69.

Figure 6:
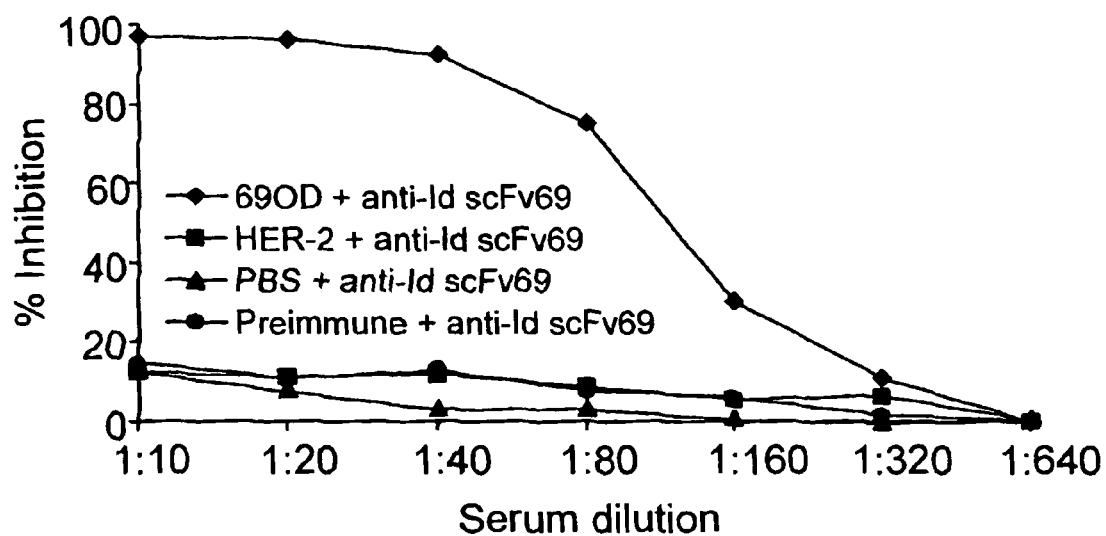

FIG. 6 is a graph that shows analysis of the Ab3 anti-anti-Id scFv 69 response in sera of BALB/c mice (immunization protocol 1) by inhibition of the binding of anti-Id scfv 69 (Ab2) on immobilized trastuzumab F(ab')$_2$ fragments (Ab1) by inhibition ELISA. Serial dilutions of preimmune sera or sera from mice each of the three groups: primed with HER-2/neu ECD-Fc fusion protein or with PBS or with anti-Id scFv 69 were preincubated with soluble anti-Id scFv 69. This solution was subsequently incubated for 2 h on trastuzumab F(ab')$_2$ fragments followed by the detection of bound scFv by HRP-conjugated M2 anti-FLAG mAb. The results obtained are expressed as percent inhibition at each serum dilution.

FIGS. 7A, 7B and 7C are graphs showing the analysis of the Ab1' response in sera of mice. Determination of anti-HER-2/neu IgG or IgM or total Ig levels in sera collected at various times after immunization with (A) soluble purified anti-Id scFv, protocol 1; (B) phage-displayed scFv, protocol 2; (C) HER-2/neu ECD-Fc fusion protein. Mice were immunized with these antigens at the indicated times (arrows). Bound antibodies in sera diluted 1:100 were detected with HRP-conjugated anti-total Ig or µ- or γ-chain specific anti-mouse Ig. Data are presented as mean±SD $A_{490}$ values of five determinations, corresponding to the five mice in each group. Curves indicate sera from mice immunized with PBS (◇), sera from mice immunized with anti-Id scFv 40 (□), sera from mice immunized with anti-Id scFv 69 (Δ), and sera from mice immunized with HER-2/neu ECD-Fc (○).

Figure 8:
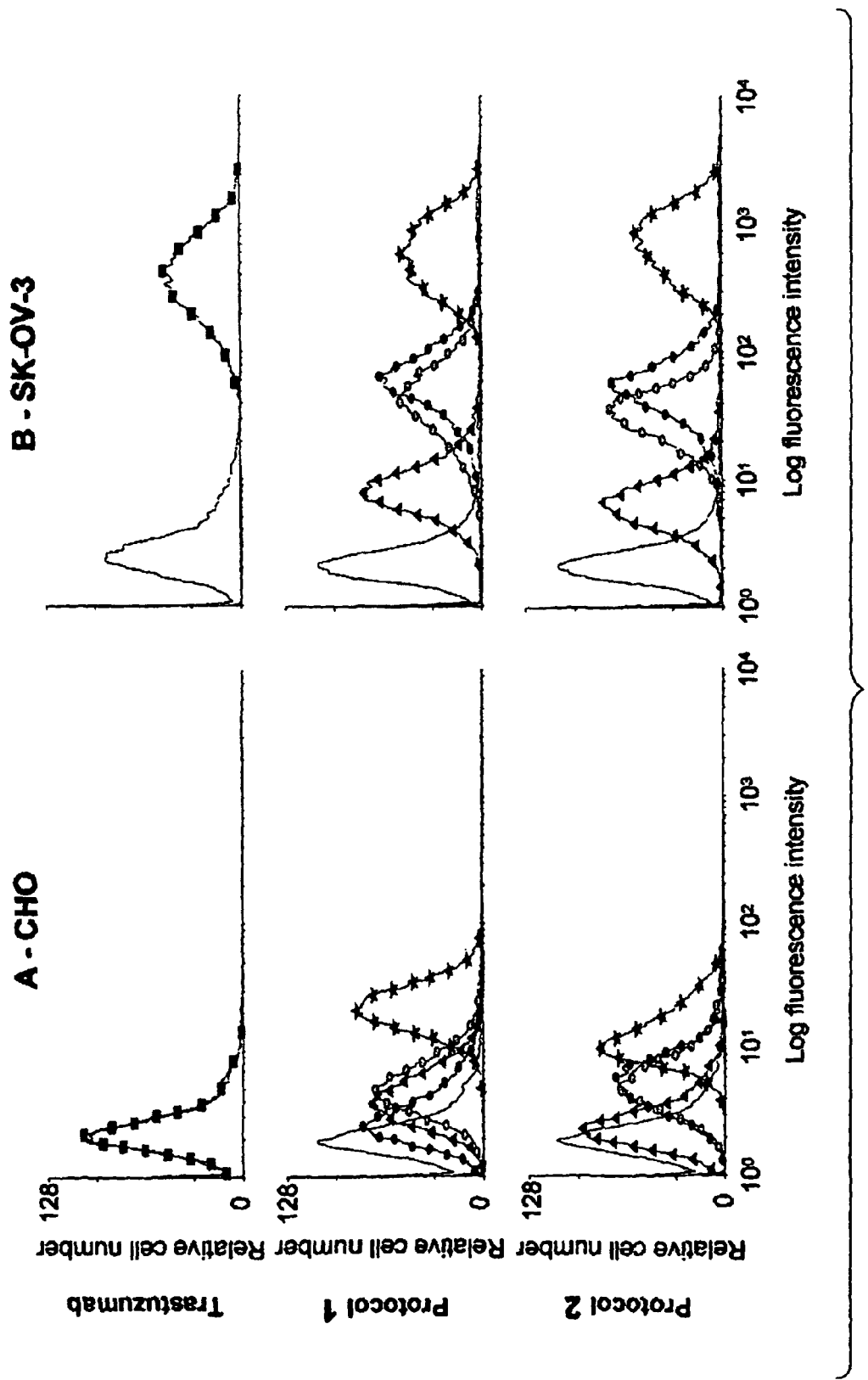

FIGS. 8A and 8B are graphs that show analysis of the binding of mouse sera to cells after the two immunization schedules: protocol 1 with soluble anti-Id scFv 40 and 69 and protocol 2 with phage-displayed scFv. The binding experiments were performed either on (A) CHO cells which do not express the HER2/neu receptor or (B) SK-OV-3-cells over-expressing HER2/neu receptor. The binding of antibodies was detected by FACS analysis using an FITC-labeled goat anti-mouse antibody. All antibody binding experiments were performed in comparison with trastuzumab detected using a FITC-labeled anti-human antibody and with the background fluorescence determined by binding on cells of the FITC-labeled secondary antibody alone. Curves indicate background fluorescence (solid line), control mAb trastuzumab (■), sera from mice immunized with PBS (▲), sera from mice immunized with anti-Id scFv 40 (☉), sera from mice immunized with anti-Id scFv 69 (●), and sera from mice immunized with HER-2/neu ECD-Fc (★).

FIG. 9 shows scFv40 and scFv69 full sequences.

EXAMPLE

Isolation and Characterization of Human Anti-Idiotypic scFv Fragment Used as a Surrogate Tumor Antigen Materials and Methods Materials The human ovarian SK-OV-3 cell line, which overexpresses HER-2/neu, and the hamster ovarian CHO cell line were obtained from American Type Culture Collection (Manassas, Va.). All the in vivo experiments were performed in compliance with the French guidelines for experimental animal studies (Agreement No. A34220). Seven-week old female BALB/c mice were obtained from Iffa Credo (L'arbresle, France). The ETH-2 synthetic human antibody phage library in the scFv format was obtained from ETH Zurich, Switzerland. This library contains more than $5 \times 10^8$ different clones. The ETH-2 library is a modified version of the synthetic antibody library of Pini et al. (Pini et al. 1998). Anti-HER-2/neu monoclonal antibody FRP5 was provided by FMI, Basel, Switzerland. Trastuzumab was purchased from Roche (F. Hoffmann-La Roche Ltd, Bazel, Switzerland). The human IgG1, used as a control, was provided by Mabgène (Alès, France). HER-2/neu ECD-Fc fusion protein, composed of two extracellular domains of the receptor linked by a human Fc fragment, was provided by Biochemistry Institute, University of Lausanne, Switzerland. Human IgG1 control and trastuzumab $F(ab')_2$ fragments were obtained by pepsin digestion (Sigma, St. Louis, Mo.) at a 3% (wt/wt) ratio of pepsin/IgG in a 0.2 M sodium acetate buffer (pH 4.0), at 37° C. for 4 h. The antibody fragments were purified by gel filtration chromatography on a Sephacryl 100 column (Amersham Biosciences, Buckinghamshire, UK). Sodium dodecyl sulfate polyacrylamide gel electrophoresis (SDS-PAGE) (8.5%), revealed more than 95% purity of the deposited proteins.

Phage Display Selection of Anti-Trastuzumab $F(ab')_2$ Fragments Anti-Id scFv Antibodies (Ab2)

Protocols for phage display panning, and analysis were as previously described (Pini et al. 1998). The phage-displayed library was panned with trastuzumab $F(ab')_2$ fragments in three sequential rounds of panning on immunotubes. Tubes were coated with trastuzumab $F(ab')_2$ fragments at a concentration of respectively 100, 50, and 10 µg/ml in PBS for all three rounds. Briefly, $5 \times 10^{12}$ phages were added to trastuzumab $F(ab')_2$ fragments, incubated under continuous rotation for 30 min followed by standing upright for an additional 1.5 h at room temperature. Tubes were extensively washed, and bound phages were eluted by addition of 1 ml 100 mM triethylamine, and then used to reinfect E. coli TG1 strain. After overnight growth, phages were isolated by polyethylene glycol precipitation and the cycle was repeated. Phage pools were assessed by ELISA. Ninety-six-well microtiter plates were coated overnight at 4° C. with 0.5 µg protein/well with either trastuzumab or human IgG1 $F(ab')_2$ fragments or anti-fd phage Ig (Sigma) in PBS. Plates were then blocked for 2 h at 37° C. with PBS/2% (w/v) non-fat dried milk. One hundred µl of serial dilutions of polyclonal phage solutions in PBS was added to each well. Plates were incubated at room temperature for 1.5 h. Bound phage-scFv were detected by reaction for 1 h 30 at 37° C. with a horseradish peroxidase (HRP)-conjugated anti-M13 mAb (Amersham Biosciences). The plates were developed using o-phenylenediamine substrate (OPD) according to the supplier's instructions (Sigma).

Production and Purification of Anti-Trastuzumab $F(ab')_2$ Fragments Soluble Anti-Id scFv After the third round of selection, E coli HB2151 cells were infected with the phages to produce soluble antibodies rather than phage-bound antibodies. Single ampicillin-resistant infected E. coli HB2151 colonies were picked in 96-well tissue culture plates and grown in 2×TY/100 µg/ml ampicillin/0.1% (w/v) glucose for 3 h at 37° C. ScFv expression was induced with isopropyl β-D-thiogalactopyranoside (IPTG) to a final concentration of 1 mM for 16 h at 30° C. The bacterial supernatants were evaluated for reactivity with trastuzumab or human IgG1 $F(ab')_2$ fragments by ELISA. The ELISA was performed as described above except that after incubation of E. coli HB2151 supernatants, bound soluble scFv was detected using HRP-conjugated anti-FLAG-tag M2 Ab (Sigma) for 1.5 h.

For Western Blot analysis, protein extracts were size fractionated by SDS-PAGE (12.5%) and electroblotted onto nitrocellulose. The blot was blocked in TBS/1% (w/v) non-fat dried milk at room temperature with shaking for 1 h, and probed with the detecting Ab (HRP-conjugated anti-FLAG-tag M2) in TBS/5% (w/v) skimmed milk at room temperature for 2 h. The blot was washed three times and developed using 4-chloro-1-naphthol as substrate (Sigma).

For each positive clone, 15 µg of plasmid DNA was purified using the NucleoSpin® Plasmid kit (Macherey-Nagel, Düren, Germany). Sequencing reactions were carried out using the Dye Terminator Sequencing kit for automatic determination of sequences with ABI PRISM 377 (Applied Biosystems, Foster City, Calif.). The primers 5'-TACTACGCAGACTCCGTGAAG-3' (SEQ ID No: 13) and 5'-GAATTTTCTGTATGAGG-3' (SEQ ID No: 14) were used for annealing.

For high scale bacterial expression and purification of scFv 39, 40, and 69, overnight cultures of E. coli HB2151 single colonies were used to inoculate 1 l of 2×YT/100 µg/ml ampicillin/0.1% (w/v) glucose and grown at 37° C. until it reached an $OD_{600}$ of 0.6. Expression of the scFvs was induced by adding 1 mM IPTG and incubating for 16 h at 30° C. Bacterial pellets were resuspended in lysis buffer (30 mM Tris-HCl (pH 7.0), 20% (w/v) sucrose, 1 mM EDTA) with 1% PMSF and cooled on ice for 30 min. After centrifugation, the supernatant (periplasmic fraction) was filtered through a 0.45 µm filter. Clear supernatant from each culture was purified using metal chelate affinity chromatography (IMAC) (30). ScFv bound on 5-ml HiTrap Ni-activated Chelating HP column (Amersham Biosciences) were eluted with 25 ml [0.02 M sodium phosphate, 0.5 M NaCl (pH 7.4)] using a linear gradient from 0 to 0.5 M imidazole, and 500-µl fractions were collected. Protein-containing fractions, monitored by $A_{280}$ densitometry, were pooled and concentrated to a volume <1 ml on Amicon Ultra 30,000 MWCO (Millipore, Bedford, Mass.). Additional purification was achieved by fast protein liquid chromatography on a gel filtration Superdex 75 column (Amersham Biosciences). The purity of the final preparation was evaluated on SDS-PAGE (12.5%). Proteins bands were detected by silver staining.

In Vitro Characterization of Anti-Id scFv by ELISA and Biacore

To characterize the anti-Id scFv, competitive ELISA experiments were carried out using either HER-2/neu ECD-Fc fusion protein to inhibit the binding of soluble scFv to trastuzumab F(ab')$_2$ fragments (Ab1) or purified scFv to block the binding of HER-2/neu ECD-Fc fusion protein to Ab1. Each soluble scFv was used at a dilution giving an $A_{490}$ of 1-1.5 in ELISA. An irrelevant soluble scFv, named Ti, isolated from the ETH-2 library and which does not bind to trastuzumab F(ab')$_2$ fragments, was used as a control (data not shown). In the first format, serial dilutions of HER-2/neu ECD-Fc fusion protein, ranging in concentration from 50 to 0 µg/ml, were used as inhibitor solutions; bound soluble scFv was detected as previously described. Recombinant human carcinoembryonic antigen (rhCEA) was used as an irrelevant inhibitor. This format of inhibition was also used immediately after the third round of selection to check the inhibition of the binding of individual periplasmic fractions on trastuzumab F(ab')$_2$ fragments by HER-2/neu ECD-Fc fusion protein. In the second format, competition was performed using various concentrations of purified soluble scFv ranging from 250 to 0 µg/ml solutions and HER-2/neu ECD-Fc fusion protein at a dilution giving an $A_{490}$ of 1-1.5 in ELISA. Bound HER-2/neu ECD-Fc fusion protein was subsequently detected with HRP-conjugated anti-HER-2/neu FRP5 mAb.

Binding experiments of anti-trastuzumab F(ab')$_2$ fragments scFv and HER-2/neu ECD-Fc fusion protein on trastuzumab F(ab')$_2$ fragments were performed at 25° C. by surface plasmon resonance analysis (SPR) using a BIACORE 2000 instrument (Biacore AB, Uppsala, Sweden). Trastuzumab F(ab')$_2$ fragments were covalently immobilized on a CM5 sensor chip surface using the amine coupling method according to the manufacturer's instructions (Biacore AB). A control reference surface was prepared using the same chemical treatment of the flow cell surface without injection of trastuzumab F(ab')$_2$ fragments. HER-2/neu ECD-Fc fusion protein (15 µg/ml) and soluble scFv (50 µg/ml) in HBS-EP buffer [10 mM HEPES (pH 7.4), 3 mM EDTA, 150 mM NaCl, 0.005% (w/v) P20] were injected over the flow cell and the dissociation phase was followed by a regeneration step (10 µl 100 mM HCl). The flow rate was 50 µl/min. All the sensorgrams were corrected by subtracting the low signal of the control reference surface. The BIA evaluation 3.2 software was used to fit the data using a 1:1 Langmuir global model. For the inhibition experiments, a first injection of anti-Id scFv 69 (50 µl at 2 µM) was followed by a second injection of HER-2/neu ECD-Fc fusion protein (50 µl at 0.06 µM). After a regeneration step with 10 µl of 100 mM HCl, a similar experiment was performed with a first injection of buffer instead of the scFv. The flow rate was 10 µl/min. To evaluate the percent inhibition, we injected the anti-Id scFv 69 followed by a long dissociation step. This dissociation curve was then subtracted from the HER-2/neu association curve.

Analysis of the Ab3 Response in Mouse Sera

Two immunization schedules were carried out. In the first one, five 6 to 8-week old female BALB/c mice per group were immunized i.p. monthly for three months with 50 µg of either purified soluble anti-Id scFv 40 or 69, 20 µg of HER-2/neu ECD-Fc fusion protein in 100 µl PBS or elution buffer (negative control group) after emulsion with complete Freund's adjuvant (CFA). Subsequent immunizations were performed i.p. with incomplete Freund's adjuvant (IFA) (protocol 1). Sera were drawn from the tail vein before each immunization and stored at −20° C. for assay. In the second one, inspired by the work of Magliani et al., 1998, 6 to 8-week old female BALB/c mice were immunized four times. A first s.c. injection of either 50 µl of freshly prepared phage-scFv 40 or 69 at a titer of $10^{14}$ TU/ml, 20 µg of HER-2/neu ECD-Fc fusion protein, or PBS was performed after emulsion with CFA. This injection was followed two weeks later by a second s.c. administration of the same dose with IFA. Two additional injections were given i.p. at 21 and 35 days after the initial immunization (protocol 2). For serum antibody measurement, mice were bled 21 and 42 days after the initial immunization and sera stored at −20° C. The sera were checked for anti-anti-Id (Ab3) responses by flow cytometry and ELISA on the HER-2/neu ECD-Fc fusion antigen as described below. Analysis of the results obtained was also performed according to the method described by Magliani et al., 1998. A positive control consisting of pooled sera from mice immunized with HER-2/neu ECD-Fc fusion protein was included in each determination. Results were expressed in arbitrary units as the ratio between absorbance of the test serum to 70% of the absorbance of the positive control serum multiplied by 1000. The 30%, subtracted from the positive control serum absorbance, was due to the anti-Fc response (see Results section).

To detect anti-anti-Id scFv in mouse sera, an ELISA was performed by coating 96-well plates with soluble anti-Id scFv at 5 µg/ml and then washing and blocking with PBS/1% (w/v) BSA for 2 h at 37° C. Serial dilutions of sera from immunized mice [1 to 1:3200 in PBS/0.5% (w/v) BSA] were incubated for 1.5 h at room temperature. Bound IgG was detected after incubation for 1.5 h of a HRP-conjugated goat anti-mouse IgG (Sigma).

To further confirm the presence of anti-anti-Id scFv, an inhibition ELISA was performed by preincubating serial dilutions of sera from immunized mice [1 to 1:640 in PBS/0.5% (w/v) BSA] with soluble scFv for 2 h at 37° C. Next, 100 µl of each mixture was added to the wells, coated with soluble anti-Id scFv. The plates were incubated at room temperature for 1.5 h. Bound scFv were detected as previously described.

ELISA and FACS Analysis of Anti-HER-2/neu Antibodies (Ab1') in Mouse Sera

Indirect ELISA was performed by coating 96-well plates overnight at 4° C. with HER-2/neu ECD-Fc fusion protein at 2 µg/ml and then blocking with PBS/1% (w/v) BSA. One hundred µl of diluted sera from mice [1:100 in PBS/0.5% (w/v) BSA] were added in each well and incubated for 1.5 h at room temperature. Then, 100 µl of either goat anti-mouse IgG (whole molecule)-HRP conjugate, goat anti-mouse IgG (γ-chain specific)-HRP conjugate, or goat anti-mouse IgM (µ-chain specific)-HRP conjugate was added, incubated for 1.5 h, and detected as described above.

For FACS analysis, HER-2/neu-positive SK-OV-3 and HER-2/neu-negative CHO cell lines were incubated for 1 h with either 100 µl of each mouse serum diluted 1:100 in PBS/1% (w/v) BSA, 1 mg/ml azide or with 100 µl trastuzumab at 20 µg/ml for 1.5 h at 4° C. After washing, the cells were incubated for another 45 min at 4° C. with either 100 µl of diluted sheep anti-mouse IgG-FITC-labeled antibody for sera or anti-human-FITC-labeled antibody (Sigma) for trastuzumab. The stained cells were suspended in 500 µl PBS, and stored at 4° C. before FACScan analysis by flow cytometry (Becton Dickinson, Franklin Lakes, Md.).

Results

The main problem when using the HER-2/neu oncoprotein as a target antigen for active immunotherapy is immune tolerance to the self-antigen. Ab1 therapy as well as peptide or protein-based vaccines have been reported (Disis et al.

2002—Pegram et al. 1998). All the studies have pointed out the necessity to pursue the search for effective therapeutic approaches.

The present study was conducted to explore the efficacy of the anti-idiotypic (Ab2) strategy to generate an anti-HER-2/neu immune response. Trastuzumab, a humanized mAb specific for HER-2/neu, whose efficiency has been proven both alone and in combination with various chemotherapeutic agents in women with HER-2-positive metastatic breast cancer (Cobleigh et al. 1999—Slamon et al. 2001), was chosen as Ab1.

The affinity selection was performed using proteolytically cleaved F(ab')$_2$ fragments of trastuzumab to avoid the selection of scFv specific for the Fc portion of the human IgG1.

Isolation of an Anti-Idiotypic scFv

The selection of the anti-Id scFv, performed by three rounds of panning of the synthetic ETH-2 scFv library on immobilized trastuzumab F(ab')$_2$ fragments (Ab1), resulted in a substantial affinity enrichment of the library on either trastuzumab or human IgG1 F(ab')$_2$ fragments (used as a control) as checked by ELISA using the recombinant polyclonal phage supernatants. A $2 \times 10^4$-fold increase of phage titer between the first and the third round of selection was also observed. After cloning, antibody supernatants derived from 96 induced individual clones of the third round were then used to infect E. coli HB2151 to produce soluble scFv antibodies. Ninety-six periplasmic fractions were tested for their reactivity with human IgG1 or trastuzumab F(ab')$_2$ fragments by ELISA. Western blot analysis of the positive periplasmic fractions led us to select scFv antibodies consisting of single monomers with the approximate molecular mass of about 30 kDa and to exclude those who presented a lower molecular mass (FIG. 1). The selected periplasmic fractions were checked by ELISA for inhibition of their binding on trastuzumab F(ab')$_2$ fragments by either HER-2/neu ECD-Fc fusion protein or rhCEA (recombinant human CEA used as an irrelevant inhibitor). Only clones showing marked inhibition (>50%) were further analyzed. After DNA sequence determination of the V$_H$ and V$_L$ regions of the antibodies, the inventors selected three unique scFv fragments termed scFv 39, 40, and 69, which recognized the binding site of Ab1 but exhibited different random loops of five or six amino acids in the CDR3 of the V$_H$ and V$_L$ domains (position 95, see Table 1).

TABLE 1

Predicted amino acid sequences of the CDR3 regions of V$_H$ and V$_L$ domains of the three unique scFv 39, 40 and 69[a]

| scFv | H-CDR3 | L-CDR3 |
|---|---|---|
| 39 | ...CAKKKIGPFDY... (SEQ ID NO: 7) | ...NSSPRPNAPVVF... (SEQ ID NO: 8) |
| 40 | ...CAKNYQIHPFDY... (SEQ ID NO: 9) | ...NSSDPDQLLVVF... (SEQ ID NO: 10) |
| 69 | ...CAKNVHIQPFDY... (SEQ ID NO: 11) | ...NSSEPTPPRVVF... (SEQ ID NO: 12) |

[a]Amino acid sequences are given in the one letter code. Random loops of 5 or 6 amino acids introduced at position 95 of V$_H$ or V$_L$ are in bold characters.

The analysis of these sequences showed that random loops appended in H-CDR3 (the largest and most diverse loop of the antigen recognition site of the antibody) for anti-Id scFv 40 and 69 presented 5/6 identical amino acids, whereas the H-CDR3 of anti-Id scFv 39 was quite different in sequence and appeared to be more positively charged. Concerning the L-CDR3, the three scFv used the DPL-16 germline gene segment, L-CDR3 of anti-Id scFv 39 differed from the others, especially from scFv 40, by a global positive charge. The L-CDR3 of scFv 69 seemed to be very highly constrained by the three proline residues in the loop.

Anti-Id scFv 39, 40, and 69 were purified to 90% homogeneity using metal chelate affinity chromatography (IMAC) followed by gel-filtration on a Superdex 75 as shown in FIG. 2 for anti-Id scFv 69. Anti-Id scFv 39 and 40 were obtained with the same level of purity. These three scFv were also expressed, displayed on phage after infection of E. coli TG1, and the immunoreactivity of each phage solution controlled by ELISA on trastuzumab F(ab')$_2$ fragments.

In Vitro Characterization of the Ab2 Anti-Idiotypic scFv

To characterize the binding properties of the anti-Id scFv, the inventors first checked whether or not these scFv exhibited competitive binding with trastuzumab F(ab')$_2$ fragments (Ab1) for HER-2/neu epitopes. When the HER-2/neu ECD-Fc fusion protein was used as an inhibitor, the binding of both anti-Id scFv 40 and 69 on trastuzumab F(ab')$_2$ fragments was inhibited by approximately 90% (FIG. 3A). The binding of anti-Id scFv 39 was only inhibited by 23%; thus, anti-Id scFv 39 was not used for subsequent experiments. The same competition experiment was performed using rhCEA (185 kDa) (FIG. 3B). Inhibition curves showed that even at high concentrations of rhCEA, this antigen (whose molecular mass is nearly the same as the HER-2/neu ECD-Fc fusion protein) was unable to compete with anti-Id scFv for the binding on trastuzumab F(ab')$_2$ fragments. Anti-Id scFv 40 and 69 were subsequently used to inhibit the binding of HER-2/neu ECD-Fc fusion protein at two different concentrations on trastuzumab F(ab')$_2$ fragments. In this format, the maximum inhibition observed was nearly 40% for anti-Id scFv 69 at 250 μg/ml (FIG. 4). The same result was obtained for anti-Id scFv 40.

Binding kinetic parameters of anti-Id scFv 40 and 69 on immobilized trastuzumab F(ab')$_2$ fragments were measured using SPR technology (FIG. 5A). Whereas the affinity constants of both scFv were in the same order of magnitude ($5 \times 10^{-6}$ M), anti-Id scFv 40 showed higher association and dissociation rates than those of scFv 69 (FIG. 5A). Under the same conditions, the affinity constant of HER-2/neu ECD-Fc fusion protein was in the nanomolar range [$K_D=(2.9\pm0.1) \times 10^{-9}$ M]. The inhibition of the binding of HER-2/neu ECD-Fc fusion protein on immobilized trastuzumab F(ab')$_2$ fragments by anti-Id scFv 69 was also evaluated using this technology. The prior injection of anti-Id scFv 69 inhibited by 83% the binding of HER-2/neu ECD-Fc fusion protein on trastuzumab F(ab')$_2$ fragments (FIG. 5B.). These results confirmed the data obtained by competitive ELISA and gave an even higher percent inhibition, suggesting that anti-Id scFv 40 and 69 could be true Ab2β. If so, these scFv should be able to induce a polyclonal anti-anti-Id response (Ab1') when injected into mice, which was further tested.

Immunizing Properties of Anti-Id scFv 40 and Anti-Id scFv 69

Six to eight-week old female BALB/c mice were immunized either i.p. with soluble purified anti-Id scFv 40 and 69 (protocol 1) or s.c. with scFv displayed on phages (protocol 2). Sera of the five mice in each group were individually tested by ELISA for their reactivity against Ab2 immunogens (anti-Id scFv 40 or 69) after three or four injections. All the mice developed significant immunity against anti-Id, and the titers were further increased with further immunizations in both protocols. Preimmune sera or control sera of mice immunized with dilution buffer (PBS or elution buffer) were tested negative against anti-Id scFv 40 and ant-Id scFv 69. No specific response was observed either in sera of mice injected with wild-type phages. To demonstrate the specificity of the Ab3 response against anti-Id scFv, an inhibition ELISA was carried out by inhibiting the binding of each anti-Id scFv on trastuzumab F(ab')$_2$ fragments by serial dilutions of sera from immunized mice. A 1:20 dilution of immune serum from a mouse immunized with anti-Id scFv 69 displayed on phage particles inhibited by nearly 100% Ab2 (anti-Id scFv 69) binding to Ab1 [trastuzumab F(ab')$_2$ fragments], suggesting that antibodies contained in the sera were true anti-anti-Id in nature (FIG. 6). Anti-Id scFv 40 gave similar results. In contrast, no inhibition was observed with immune sera from mice immunized with HER-2/neu ECD-Fc fusion protein or PBS.

Idiotype Analysis of Ab3 (Ab1') Induced by Immunization with Anti-Id scFv

Figure 7:
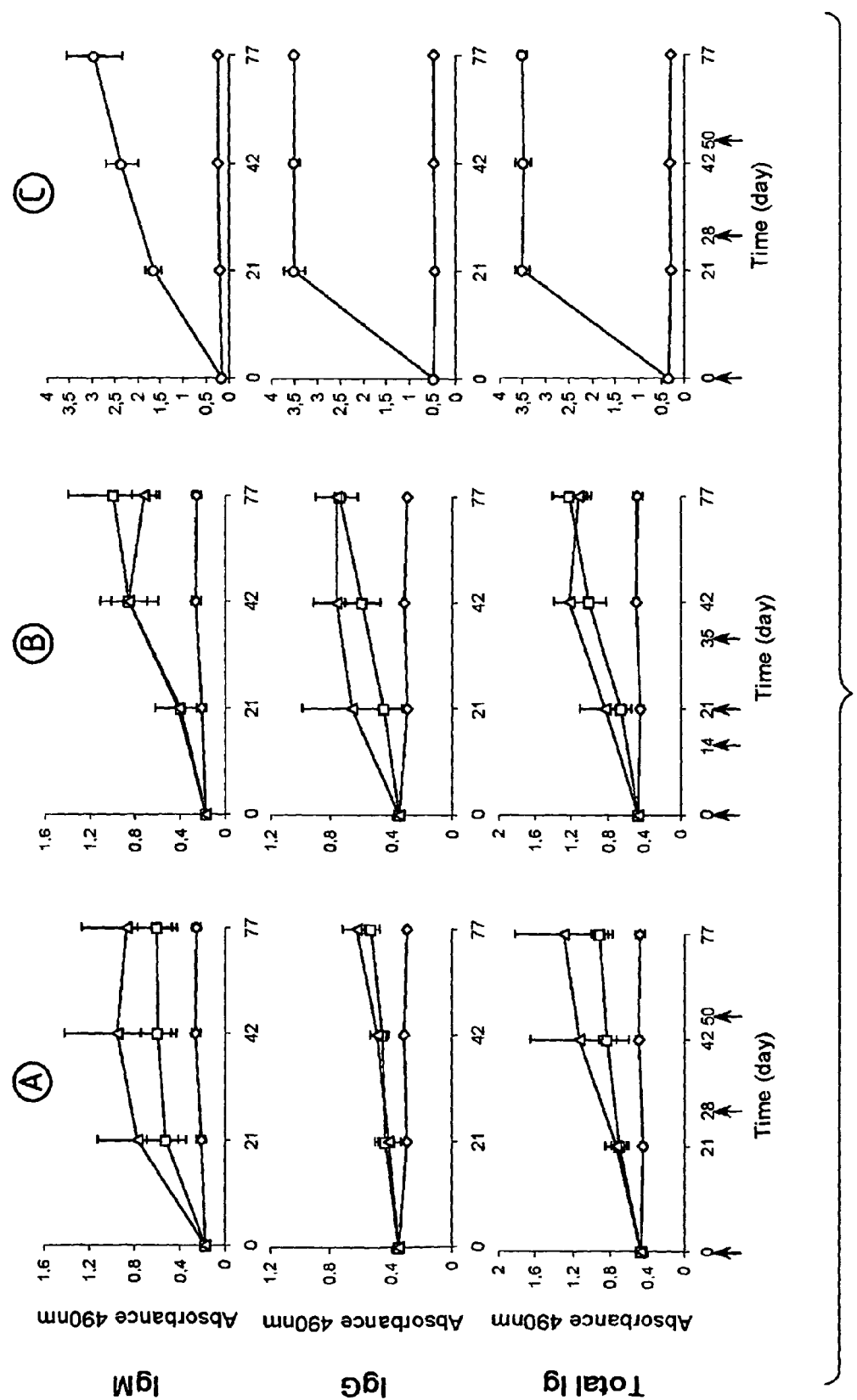

To detect the subset of antibodies called Ab1', able to bind to the target antigen, ELISA were performed on HER-2/neu ECD-Fc fusion protein using mouse sera diluted 1:100. The use of different HRP-conjugated Ig allowed us to determine the IgG, IgM, and total Ig levels induced in mouse sera by immunization with anti-Id scFv and control immunogens (FIG. 7). The absorbance values plotted at each time correspond to the mean value for each group of five mice±standard deviations (SD). These results demonstrated that (i) patterns of induction of IgG or IgM anti-HER-2/neu antibodies were similar for the two immunization protocols (FIGS. 7A and B); (ii) a significant portion of the polyclonal Ab3 reacted with the antigen (FIGS. 7A and B), the level of Ab1' reaching a plateau after 3-4 injections of immunogen; and (iii) as shown in FIG. 7C, the titers of IgM as well as IgG anti-HER-2/neu ECD-Fc fusion protein response were, as expected, very high in the sera of mice immunized with HER-2/neu ECD-Fc fusion protein, whereas there was no reactivity in the negative control. In the sera of mice immunized with HER-2/neu ECD-Fc fusion protein, part of the very high titer against the adsorbed protein was due to an anti-human Fc response as shown when the reactivity of the positive anti-HER-2/neu ECD-Fc fusion protein sera against another recombinant Fc fusion protein, the so-called MICA-Fc, provided by LICR, Lausanne Branch) was checked by ELISA. The data obtained led the inventors to conclude that the anti-Fc response was about 30% of the total response observed by ELISA on HER-2/neu ECD-Fc fusion protein.

Flow Cytometric Analysis of Ab1'

To further confirm the nature of the Ab1' induced by injections with anti-Id scFv 40 and 69, flow cytometric analyses of HER-2/neu-positive SK-OV-3 cells and HER-2/neu-negative CHO cells were performed with sera (1:100) from immunized BALB/c mice. Using trastuzumab mAb, both HER-2/neu overexpression at the surface of SK-OV-3 cells and the lack of expression of the receptor on the CHO cells surface were first confirmed (FIGS. 8A and B). Then, the inventors demonstrated that antibodies not only in sera from mice immunized with HER-2/neu ECD-Fc fusion protein but also in sera from mice immunized either with anti-Id scFv 40 or anti-Id scFv 69, specifically stained the SK-OV-3 cells. Only a weak reactivity was observed on CHO cell line. Representative results obtained at the end of the two immunization schedules are presented also in FIGS. 8A and B. The fluorescence intensity increase on SK-OV-3 cells, as compared with CHO cells, were about 100, 25, and 2 for sera from mice immunized with HER-2/neu ECD-Fc fusion protein, anti-Id scFv 40 or 69, and PBS, respectively. The staining of cells obtained by using sera from mice injected with dilution buffer was equivalent to that of preimmune sera, thus corresponding to the background signal. On the basis of these experiments, the inventors concluded that true Ab1' antibodies, which are specifically directed against the HER-2/neu receptor, were present in the sera of mice immunized with anti-Id scFv 40 and 69.

REFERENCES

Baral, R., A. Sherrat, R. Das, K. A. Foon, and M. Bhattacharya-Chatterjee. 2001. Murine monoclonal anti-idiotypic antibody as a surrogate antigen for human Her-2/neu. *Int J Cancer* 92:88.

Baselga, J., and J. Albanell. 2001. Mechanism of action of anti-HER2 monoclonal antibodies. *Ann Oncol* 12:S35.

Bhattacharya-Chatterjee, M., S. K. Chatterjee, S. Vasile, B. K. Seon, and H. Kohler. 1988. Idiotype vaccines against human T cell leukemia. II. Generation and characterization of a monoclonal idiotype cascade (Ab1, Ab2, and Ab3). *J Immunol* 141:1398.

Cobleigh, M. A., C. L. Vogel, D. Tripathy, N. J. Robert, S. Scholl, L. Fehrenbacher, J. M. Wolter, V. Paton, S. Shak, G. Lieberman, and D. J. Slamon. 1999. Multinational study of the efficacy and safety of humanized anti-HER2 monoclonal antibody in women who have HER2-overexpressing metastatic breast cancer that has progressed after chemotherapy for metastatic disease. *J Clin Oncol* 17:2639.

Concetti, A., A. Amici, C. Petrelli, A. Tibaldi, M. Provinciali, and F. M. Venanzi. 1996. Autoantibody to p185erbB2/neu oncoprotein by vaccination with xenogenic DNA. *Cancer Immunology, Immunotherapy* 43:307.

Dakappagari, N. K., D. B. Douglas, P. L. Triozzi, V. C. Stevens, and P. T. Kaumaya. 2000. Prevention of mammary tumors with a chimeric HER-2 B-cell epitope peptide vaccine. *Cancer Res* 60:3782.

Di Carlo, E., S. Rovero, K. Boggio, E. Quaglino, A. Amici, A. Smorlesi, G. Forni, and P. Musiani. 2001. Inhibition of mammary carcinogenesis by systemic interleukin 12 or p185neu DNA vaccination in Her-2/neu transgenic BALB/c mice. *Clin Cancer Res* 7:830s.

Disis, M. L., E. Calenoff, G. McLaughlin, A. E. Murphy, W. Chen, B. Groner, M. Jeschke, N. Lydon, E. McGlynn, R. B. Livingston, and et al. 1994. Existent T-cell and antibody immunity to HER-2/neu protein in patients with breast cancer. *Cancer Res* 54:16.

Disis, M. L., F. M. Shiota, and M. A. Cheever. 1998. Human HER-2/neu protein immunization circumvents tolerance to rat neu: a vaccine strategy for 'self' tumour antigens. *Immunology* 93:192.

Disis, M. L., J. R. Gralow, H. Bernhard, S. L. Hand, W. D. Rubin, and M. A. Cheever. 1996. Peptide-based, but not whole protein, vaccines elicit immunity to HER-2/neu, oncogenic self-protein. *J Immunol* 156:3151.

Disis, M. L., T. A. Gooley, K. Rinn, D. Davis, M. Piepkorn, M. A. Cheever, K. L. Knutson, and K. Schiffman. 2002. Generation of T-cell immunity to the HER-2/neu protein after active immunization with HER-2/neu peptide-based vaccines. *J Clin Oncol* 20:2624.

Fisk, B., T. L. Blevins, J. T. Wharton, and C. G. Ioannides. 1995. Identification of an immunodominant peptide of HER-2/neu protooncogene recognized by ovarian tumor-specific cytotoxic T lymphocyte lines. *J Exp Med* 181:2109.

Foon, K. A., J. Lutzky, R. N. Baral, J. R. Yannelli, L. Hutchins, A. Teitelbaum, O. L. Kashala, R. Das, J. Garrison, R. A. Reisfeld, and M. Bhattacharya-Chatterjee. 2000. Clinical and immune responses in advanced melanoma patients immunized with an anti-idiotype antibody mimicking disialoganglioside GD2. *J Clin Oncol* 18:376.

Foon, K. A., W. J. John, M. Chakraborty, R. Das, A. Teitelbaum, J. Garrison, O. Kashala, S. K. Chatterjee, and M. Bhattacharya-Chatterjee. 1999. Clinical and Immune Responses in Resected Colon Cancer Patients Treated With Anti-Idiotype Monoclonal Antibody Vaccine That Mimics the Carcinoembryonic Antigen. *J Clin Oncol* 17:2889.

Goletz et al. (2002), J. Mol. Biol. 315:1087

Jerne, N. K. 1974. Towards a network theory of the immune system. *Ann Immunol (Paris)* 125C:373.

Jerne et al.; (1982) EMBO, 1:1234

Kennedy, R. C., G. R. Dreesman, J. S. Butel, and R. E. Lanford. 1985. Suppression of in vivo tumor formation induced by simian virus 40-transformed cells in mice receiving antiidiotypic antibodies. *J Exp Med* 161:1432.

de Kruif and Logtenberg (1996) Journal of biological chemistry vol. 271, no 13, 7630-7634

Kwak, L. W., M. J. Campbell, D. K. Czerwinski, S. Hart, R. A. Miller, and R. Levy. 1992. Induction of immune responses in patients with B-cell lymphoma against the surface-immunoglobulin idiotype expressed by their tumors. *N Engl J Med* 327:1209.

Leung et al. (2000) Gene 373-380

Mac Cluskie and Weeratna, (2001) Curr Drug Targets Infect Disord. 1(3):263-71

Magliani, W., L. Polonelli, S. Conti, A. Salati, P. F. Rocca, V. Cusumano, G. Mancuso, and G. Teti. 1998. Neonatal mouse immunity against group B streptococcal infection by maternal vaccination with recombinant anti-idiotypes [see comments]. *Nat Med* 4:705.

Maniatis et al. (1982) Molecular cloning: a laboratory manual, Cold Spring Harbor Laboratories, NY, 51-54 and 412-30

Merrifield, (1962) Proc. Soc. Ex. Boil. 21:412

Merrifield, (1963) J. Am. Chem. Soc. 85:2149

Miller et al., (2003) Journal of immunology 170:4854-4861

Mittelman, A., Z. J. Chen, T. Kageshita, H. Yang, M. Yamada, P. Baskind, N. Goldberg, C. Puccio, T. Ahmed, Z. Arlin, and et al. 1990. Active specific immunotherapy in patients with melanoma. A clinical trial with mouse antiidiotypic monoclonal antibodies elicited with syngeneic anti-high-molecular-weight-melanoma-associated antigen monoclonal antibodies [published erratum appears in J Clin Invest 1991 February; 87(2):757]. *Journal of Clinical Investigation* 86:2136.

Nanda, N. K., and E. E. Sercarz. 1995. Induction of anti-self-immunity to cure cancer. *Cell* 82:13.

Pack et al., (1993) Biotechnology 11:1271-7

Pegram, M. D., A. Lipton, D. F. Hayes, B. L. Weber, J. M. Baselga, D. Tripathy, D. Baly, S. A. Baughman, T. Twaddell, J. A. Glaspy, and D. J. Slamon. 1998. Phase II study of receptor-enhanced chemosensitivity using recombinant humanized anti-p185HER2/neu monoclonal antibody plus cisplatin in patients with HER2/neu-overexpressing metastatic breast cancer refractory to chemotherapy treatment. *J Clin Oncol* 16:2659.

Peoples, G. E., P. S. Goedegebuure, R. Smith, D. C. Linehan, I. Yoshino, and T. J. Eberlein. 1995. Breast and ovarian cancer-specific cytotoxic T lymphocytes recognize the same HER2/neu-derived peptide. *Proc Natl Acad Sci USA* 92:432.

Pilon, S. A., M. P. Piechocki, and W. Z. Wei. 2001. Vaccination with cytoplasmic ErbB-2 DNA protects mice from mammary tumor growth without anti-ErbB-2 antibody. *J Immunol* 167:3201.

Pini, A., F. Viti, A. Santucci, B. Carnemolla, L. Zardi, P. Neri, and D. Neri. 1998. Design and use of a phage display library. Human antibodies with subnanomolar affinity against a marker of angiogenesis eluted from a two-dimensional gel. *J Biol Chem* 273:21769.

Reeck et al, 1987, Cell, 50 : 667.

Rilke, F., M. I. Colnaghi, N. Cascinelli, S. Andreola, M. T. Baldini, R. Bufalino, G. Della Porta, S. Menard, M. A. Pierotti, and A. Testori. 1991. Prognostic significance of HER-2/neu expression in breast cancer and its relationship to other prognostic factors. *Int J Cancer* 49:44.

Saha et al., (2003) Cancer Res 63:2844-54

Sambrook et al, 1989, Molecular Cloning: A laboratory manual, second edition Cold Spring Harbor Laboratory press, Cold Spring Harbor, New-York.

Slamon, D. J., B. Leyland-Jones, S. Shak, H. Fuchs, V. Paton, A. Bajamonde, T. Fleming, W. Eiermann, J. Wolter, M. Pegram, J. Baselga, and L. Norton. 2001. Use of chemotherapy plus a monoclonal antibody against HER2 for metastatic breast cancer that overexpresses HER2. *N Engl J Med* 344:783.

Tam et al., (1983) J. Am. Chem. Soc. 105:6442

Tripathi, P. K., H. Qin, S. Deng, C. Xu, M. Bhattacharya-Chatterjee, K. A. Foon, and S. K. Chatterjee. 1998. Antigen mimicry by an anti-idiotypic antibody single chain variable fragment. *Mol Immunol* 35:853.

Winter et al., 1994, Annu. Rev. Immunol., 12, 433

---

The invention claimed is:

1. An isolated human anti-idiotypic antibody Fab- or scFv-fragment, which mimics Her-2/neu tumor associated antigen, and which comprises CDR1H, CDR1L, CDR2H, CDR2L, CDR3H and CDR3L, wherein the amino acid sequence of CDR1H consists of the sequence SYAMS (SEQ ID No: 15), wherein the amino acid sequence of CDR1L consists of the sequence QGDSLRSYYAS (SEQ ID No: 16), wherein the amino acid sequence of CDR2H consists of the sequence SGGTYYADSVKG (SEQ ID No: 17), wherein the amino acid sequence of CDR2L consists of the sequence GKNNRPS (SEQ ID No: 18), and (i) wherein the amino acid sequence of CDR3H consists of the sequence SEQ ID No: 3 when the amino acid sequence of CDR3L consists of the sequence SEQ ID No: 4, or (ii) wherein the amino acid sequence of CDR3H consists of the sequence SEQ ID No: 5 when the amino acid sequence of CDR3L consists of the sequence SEQ ID No: 6, wherein said fragment binds trastuzumab F(ab')$_2$.

2. The fragment of claim 1, wherein CDR3H consists of SEQ ID No: 3 and CDR3L consists of SEQ ID No: 4.

3. The fragment of claim 2, which comprises the amino acid sequence SEQ ID No: 1, this fragment being designated scFv40.

4. The fragment of claim 1, wherein CDR3H consists of SEQ ID No: 5 and CDR3L consists of SEQ ID No: 6.

5. The fragment of claim 4, which comprises the amino acid sequence SEQ ID No: 2, this fragment being designated scFv69.

6. A multimer of the antibody fragment defined in claim 1.

7. A pharmaceutical composition comprising an antibody fragment according to claim 1, or a multimer of the antibody fragment, in association with a pharmaceutically acceptable carrier.

8. An isolated human anti-idiotypic antibody Fab- or ScFv-fragment, which mimics Her-2/neu tumor associated antigen, wherein said fragment comprises the amino acid sequence SEQ ID No: 1, this fragment being designated scFv40, wherein said fragment binds to trastuzumab F(ab')$_2$.

9. A multimer of the antibody fragment defined in claim 8.

10. A pharmaceutical composition comprising an antibody fragment according to claim 8, or a multimer of the antibody fragment, in association with a pharmaceutically acceptable carrier.

11. An isolated human anti-idiotypic antibody Fab- or ScFv-fragment, which mimics Her-2/neu tumor associated antigen, wherein said fragment comprises the amino acid sequence SEQ ID No: 2, this fragment being designated scFv69, wherein said fragment binds to trastuzumab F(ab')$_2$.

12. A multimer of the antibody fragment defined in claim 11.

13. A pharmaceutical composition comprising an antibody fragment according to claim 11, or a multimer of the antibody fragment, in association with a pharmaceutically acceptable carrier.

* * * * *